United States Patent [19]

Parsons et al.

[11] Patent Number: 5,173,503
[45] Date of Patent: Dec. 22, 1992

[54] IMIDAZOLE FUNGICIDES

[75] Inventors: John H. Parsons, Saffron Walden; Russell G. Hunt, Cambridge; Kenneth Hamilton, Cambridge; Dale R. Mitchell, Cambridge, all of England

[73] Assignee: Schering Agrochemicals Limited, England

[21] Appl. No.: 606,699

[22] Filed: Oct. 31, 1990

[30] Foreign Application Priority Data

Nov. 15, 1989 [GB] United Kingdom ................. 8925790
Aug. 11, 1990 [GB] United Kingdom ................. 9017640

[51] Int. Cl.$^5$ .................... A01N 43/50; C07D 233/90
[52] U.S. Cl. .................... 514/398; 514/397; 548/315.1; 548/316.7
[58] Field of Search ................. 548/337, 336; 514/398, 514/397

[56] References Cited

U.S. PATENT DOCUMENTS 4,995,898 2/1991 Nasu et al. .................... 548/337

5,045,557 9/1991 Buss et al. .................... 514/398

FOREIGN PATENT DOCUMENTS 284277 9/1988 European Pat. Off. .

Primary Examiner—Patricia L. Morris
Attorney, Agent, or Firm—Ostrolenk, Faber, Gerb & Soffen

[57] ABSTRACT

Compounds of formula I

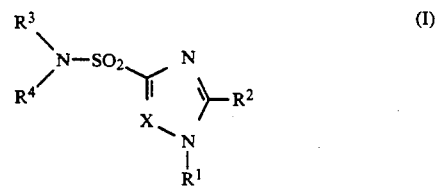

in which X and $R^{1-4}$ have the meanings given in the description, have activity against phytopathogenic fungi.

19 Claims, No Drawings

IMIDAZOLE FUNGICIDES

This invention relates to compounds having fungicidal activity.

In our EP 284 277, disclosed fungicidal compounds of formula

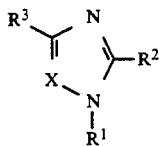

in which
X is $CR^4$ or N;
$R^1$ is $-SO_2R^5$,

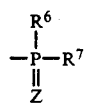

or $-COR^8$
$R^2$ is CN,

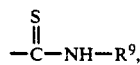

$-CH=N-OR^{10}$,

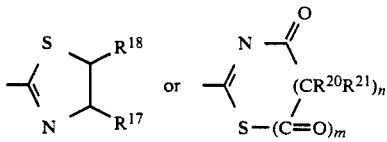

$R^3$ and $R^4$, may be the same or different and are alkyl, cycloalkyl, cycloalkenyl, alkenyl, alkynyl or amino, all of which are optionally substituted, hydrogen, halogen, hydroxy, cyano, nitro, acyl, $R^{11}SO_p$, $R^{12}O$ or aryl;

$R^5$ is aryl, optionally substituted alkyl or optionally substituted amino;

$R^6$ and $R^7$, may be the same or different and are amino, alkoxy or alkylthio, each of which is optionally substituted;

$R^8$ has the same meaning as $R^5$ or can be alkoxy, alkenyloxy, alkynyloxy or alkylthio, each of which is optionally substituted, or is aryloxy;

$R^9$ is hydrogen, optionally substituted alkyl, alkenyl, alkynyl, alkoxycarbonyl, acyl, aryl or cycloalkyl;

$R^{10}$ is hydrogen, optionally substituted alkyl, alkenyl or alkynyl;

$R^{11}$ is alkyl, cycloalkyl, cycloalkenyl, alkenyl, alkynyl, all of which are optionally substituted, or is aryl;

$R^{12}$ has the same meaning as $R^{11}$ or is acyl;

$R^{17}$ is hydrogen, alkyl, alkoxycarbonyl, aryl or heteroaryl and $R^{18}$ is hydrogen or alkyl or $R^{17}$ and $R^{18}$ together with the carbons to which they are attached, form a benzo ring;

$R^{20}$ and $R^{21}$ may be the same or different and are hydrogen or alkyl;

Z is oxygen or sulphur;

m is 0 and n is 1 or 2 or m is 1 and n is 0 or 1; and
p is 0 or 1.

In that patent, in most of the exemplified compounds, the $R^3$ group is a (substituted) phenyl. However, it is stated that $R^3$ can be acyl and that acyl includes groups such as N,N-dialkylsulphamoyl and N-alkyl-N-arylsulphamoyl. Two such compounds are exemplified.

In EP 298 196, there are disclosed similar types of 1-sulphamoyl-2-cyanoimidazoles to those disclosed in EP 284 277. In this patent application, there are claimed inter alia compounds having a di-$C_{1-4}$-alkylsulphamoyl group in the 4 position. One compound of this type is exemplified.

We have now found that a particular group of compounds of this type having defined sulphamoyl substituents have particularly valuable properties.

According to the invention there is provided a compound of formula I

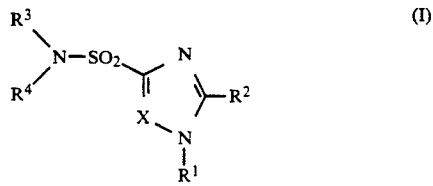 (I)

in which
X is $CR^6$ or N;
$R^1$ is $-SO_2R^7$
$R^2$ is CN or

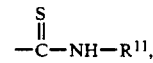

$R^3$ and $R^4$ together with the nitrogen to which they are attached form a 5 to 7 membered ring which is optionally substituted and optionally contains other hetero atoms; or $R^4$ is the group $Ar-W_n-$, W is an optionally substituted alkylene or alkenylene group, and either a) n is 1 and $R^3$ is alkyl, alkenyl or alkynyl, each of which are optionally substituted, or is Ar, or b) n is 0 and $R^3$ is Ar;

Ar is aryl;

$R^6$ is alkyl, cycloalkyl, cycloalkenyl, alkenyl, alkynyl or amino, all of which are optionally substituted, hydrogen, halogen, hydroxy, cyano, nitro, acyl, $R^{13}SO_p$, $R^{14}O$ or aryl;

$R^7$ is aryl, optionally substituted alkyl or optionally substituted amino;

$R^{11}$ is hydrogen, optionally substituted alkyl, alkenyl, alkynyl, alkoxycarbonyl, acyl, aryl or cycloalkyl;

$R^{12}$ is hydrogen, or optionally substituted alkyl, alkenyl or alkynyl;

$R^{13}$ is alkyl, cycloalkyl, cycloalkenyl, alkenyl, alkynyl, all of which are optionally substituted, or is aryl;

$R^{14}$ has the same meaning as $R^{13}$ or is acyl; and
p is 0 or 1.

Where $R^3$ and $R^4$ form a ring and the ring is substituted, two substituents can form a ring fused to the first ring. In such circumstances, it is generally preferred that $R^3$ and $R^4$ form a saturated ring to which is fused an optionally substituted benzo ring. Other substituents include $C_{1-4}$-alkyl.

W is of a chain length of 1 to 6 carbon atoms, e.g. 1 or 2 carbon atoms. When it is substituted, the substituents can include one or more of the same or different alkyl, alkenyl or alkynyl groups, each of which are optionally substituted, halogen or aryl.

Ar is preferably phenyl, optionally substituted by halogen, $C_{1-4}$alkyl, $C_{1-4}$-alkoxy, $C_{1-4}$-alkylthio, $C_{1-4}$-alkylsulphinyl, $C_{1-4}$-alkylsulphonyl or $C_{1-4}$-dialkylamino, or is thienyl.

It is generally preferred that R: is the group $Ar\text{-}W_n\text{-}$, and that W is methylene or ethylene, especially methylene, and n is 1. In such circumstances, $R^3$ is preferably $C_{1-4}$-alkyl, especially methyl.

In a preferred group of compounds:
X is CH;
$R^1$ is dimethylsulphamoyl and
$R^2$ is cyano;

Alkyl groups are preferably of 1 to 8 carbon atoms, especially methyl; alkenyl and alkynyl groups are usually of 3 to 4 carbon atoms and cycloalkyl and cycloalkenyl groups are usually of 3 to 8 carbon atoms. Substituents, when present on any such group, include halogen, hydroxy, alkoxy and aryl. Aryl groups are usually phenyl, optionally substituted, e.g. by halogen, alkyl, alkoxy, nitro, cyano, acyl, optionally substituted amino, alkyl-$SO_q$, or aryl-$SO_q$, where q is 0 or 1, and any alkyl or alkoxy group is optionally substituted.

The term aryl may include heteroaryl groups such as thienyl, furyl or pyridyl and can also include polynuclear aromatic groups, such as naphthyl and benzimidazolyl. Amino groups are usually substituted by one or more of the groups $R^{13}$, acyl, optionally substituted amino (including groups substituted through a double bond), hydroxy or optionally substituted alkoxy, or the two substituents can form a ring, e.g. a morpholino or piperidino ring. Sulphamoyl groups can be substituted similarly to amino groups. The term acyl can include residues of both carboxylic and sulphonic acids and includes the groups $R^{15}(O)_rCO$ and $R^{15}SO_2$, where $R^{15}$ has the same meaning as $R^{13}$, or is optionally substituted amino and r is 0 or 1. It thus includes residues of carbamic and sulphamic acids. Acyl groups are preferably alkanoyl, aroyl, alkylsulphonyl, arylsulphonyl, N,N-dialkylsulphamoyl, N,N-diarylsulphamoyl or N-alkyl-N-aryl-sulphamoyl, in which the alkyl groups are e.g. of 1 to 4 carbon atoms, and the alkyl and aryl can be substituted as previously mentioned.

The compounds of the invention have activity as fungicides, especially against fungal diseases of plants, e.g. downy mildews, especially vine downy mildew (*Plasmopara viticola*), and late tomato blight and potato blight (*Phytophthora infestans*). They are also active against powdery mildews, such as barley powdery mildew (*Erysiphe graminis*), as well as being active against diseases such as rice blast (*Pyricularia oryzae*) and apple scab (*Venturia inaequalis*). They may also have activity against other fungi, such as Botrytis spp., Puccinia spp., Rhizoctonia spp., Fusarium spp. and Pythium spp..

The invention thus also provides a method of combating fungi at a locus infested or liable to be infested therewith, which comprises applying to the locus a compound of formula I.

The invention also provides an agricultural composition comprising a compound of formula I in admixture with an agriculturally acceptable diluent or carrier. The composition of the invention may of course include more than one compound of the invention.

In addition the composition can comprise one or more additional active ingredients, for example compounds known to possess plant-growth regulant, herbicidal, fungicidal, insecticidal or acaricidal properties. Alternatively the compounds of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkyl-naphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyne-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a fumigant, a smoke, a dispersible powder, an emulsifiable concentrate or granules. Moreover it can be in a suitable form for direct application or as a concentrate or primary composition which requires dilution with a suitable quantity of water or other diluent before application.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The concentration of the active ingredient in the composition of the present invention, as applied to plants is preferably within the range of 0.0001 to 1.0 per cent by weight, especially 0.0001 to 0.01 per cent by weight. In a primary composition, the amount of active ingredient can vary widely and can be, for example, from 5 to 95 per cent by weight of the composition.

In the method of the invention the compound is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.05 to 5 kg per hectare, more preferably from 0.1 to 1 kg per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.01 to 10 kg per hectare, preferably from 0.05 to 5 kg per hectare.

The compounds of the invention may be prepared, in known manner, in a variety of ways.

For example, the compounds in which $R^2$ is cyano, may be prepared by cyanating a compound of formula II

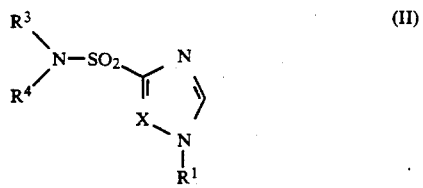

(II)

Cyanation can be achieved for instance by reacting the relevant compound with a compound Z-CN, where Z is a leaving group such as cyano, p-tosyl or phenoxy. This reaction is generally carried out in the presence of a strong base and preferably an alkyl metal, such as butyllithium. The cyanation can also be carried out by (i) formylating an uncyanated compound, (e.g. using dimethylformamide in the presence of strong base, such as butyllithium) to give a compound having a formyl group (ii) treating this compound with hydroxylamine and (iii) subsequently dehydrating the oxime so obtained. Dehydration may be achieved using a reagent such as trifluoroacetic anhydride or a chloroformate ester, under alkaline conditions. In the latter case an ester group may be substituted onto the 1-position.

Compounds of formula I, where $R^2$ is cyano, can be modified in known manner to give compounds where $R^2$ is thiocarbamoyl, by reaction with hydrogen sulphide and if desired modifying this group in known manner to give compounds where $R^9$ is not hydrogen. These reactions are usually carried out using a suitable acyl halide or isocyanate, for instance as described in EP 219192.

Compounds of formula II are known or can be obtained in known manner. For example a compound of formula III

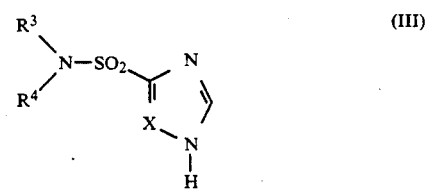

(III)

is reacted with a compound of formula $R^1Q$, where Q is a leaving group, such as halogen, especially chlorine. Compounds of formula III are known or can be obtained in a variety of known ways, for instance using methods as described for the preparation of starting materials hereinafter.

Alternatively, where $R^4$ is $Ar-W_n$-, a compound of formula IV

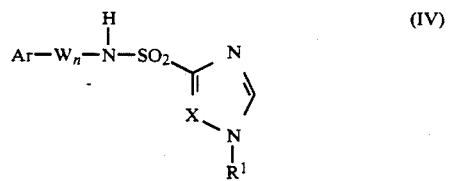

(IV)

can be reacted with a compound of formula $R^3Q$, where Q is a leaving group, such as halogen, especially bromine or iodine, to give the compound of formula II.

The compounds of formula III, where $R^4$ is $Ar-W_n$-, and compounds of formula IV can be obtained for example according to the following reaction scheme.

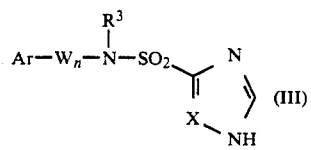

(III)

-continued

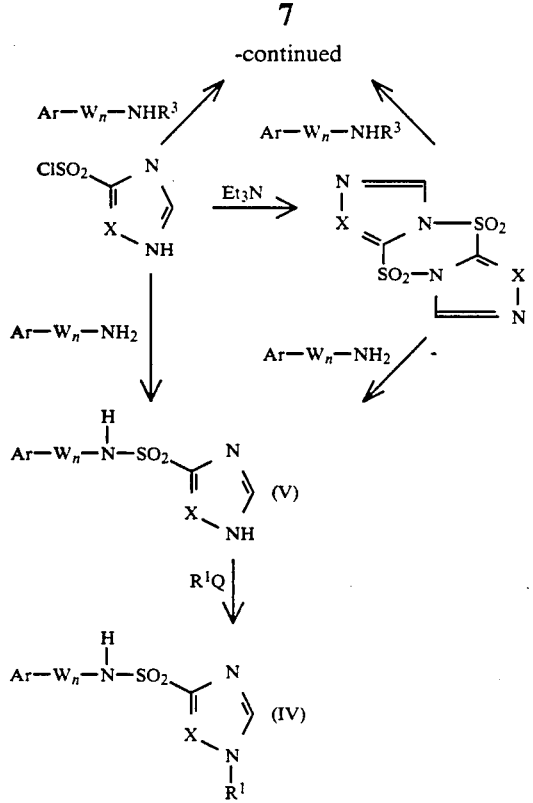

Sulphamoylation and similar reactions can be carried out, under basic conditions, e.g. in the presence of potassium carbonate or sodium hydride. The reaction with $R^3Q$ is generally carried out under similar conditions to the sulphamoylation.

Compounds where Ar comprises a sulphinyl or sulphonyl substituent can be obtained by oxidising a compound comprising the equivalent thio substituent with a suitable oxidising agent such as m-chloroperbenzoic acid.

The invention is illustrated in the following Examples. Structures of isolated novel compounds were confirmed by elemental and/or other appropriate analyses. Temperatures are in °C and are uncorrected.

EXAMPLE 1

To a solution of N,N-dimethyl-4-(1,2,3,4-tetrahydroisoquinolin-2-ylsulphonyl)-1H-imidazole-1-sulphonamide (9 g) in dry tetrahydrofuran (120 ml) at −70° under a dry nitrogen atmosphere was added 2.5M butyllithium in hexane (8 ml). After stirring for 15 mins, the temperature was allowed to rise to −20° and redistilled tosyl cyanide (2.38 g) was added and the reaction flask placed in an ice bath. The mixture was stirred for 1 hour, poured into water and the precipitate filtered and purified by silica gel column chromatography and recrystallisation from ethyl acetate/hexane to give 2-cyano-N,N-dimethyl-4-(1,2,3,4-tetrahydroisoquinolin-2-ylsulphonyl)-1H-imidazole-1-sulphonamide, mp 143°–144°. (compound 1)

The starting material was prepared as follows:

A solution of 1,2,3,4-tetrahydroisoquinoline (13.22 g) and imidazole-4-sulphonyl chloride (7.57 g) in toluene (70 ml) was stirred for 1 hour and then allowed to stand overnight. It was evaporated and the residue partitioned between diethyl ether and aqueous sodium hydroxide. The aqueous layer was clarified by ether extraction and then acidified with concentrated hydrochloric acid. The precipitate was collected, washed with water and dried to give crude 4-(1,2,3,4-tetrahydroisoquinolin-2-ylsulphonyl)-1H-imidazole. A solution of this product (9 g) in dimethylformamide was treated with sodium hydride (1.13 g of 80% in oil), followed by dimethylsulphamoyl chloride (5.4 g). The mixture was stirred for 1 hour and poured into water. The precipitate was collected and worked up to give the starting material.

EXAMPLE 2

In a similar manner, the following compounds were obtained:
a) 2-cyano-N,N-dimethyl-4-(indolin-1-ylsulphonyl)-1H-imidazole-1-sulphonamide, mp 155°–158°. (compound 2)
b) 2-cyano-N,N-dimethyl-4-(1,2,3,4-tetrahydroquinolin-1-ylsulphonyl)-1H-imidazole-1-sulphonamide, mp 159°–161.5°. (compound 3)
c) 2-cyano-N,N-dimethyl-4-[(2-methylindolin-1-yl)sulphonyl]-1H-imidazole-1-sulphonamide, mp 157°–158°. (compound 4)
d) 2-cyano-N,N-dimethyl-4-(morpholinosulphonyl)-1H-imidazole-1-sulphonamide, mp 206°–208°. (compound 5)
e) 2-cyano-N,N-dimethyl-4-[(4-benzylpiperazino)sulphonyl]-1H-imidazole-1-sulphonamide, mp 166°–168°. (compound 6)
f) 2-cyano-N,N-dimethyl-4-[(4-phenylpiperazino)sulphonyl]-1H-imidazole-1-sulphonamide, mp 168°–171°. (compound 7)

EXAMPLE 3

To a solution of $N^4$-(4-chlorobenzyl)-$N^1,N^1,N^4$-trimethyl-1H-imidazole-1,4-disulphonamide, (20 g) in dry tetrahydrofuran (180 ml) at −78°, under a dry nitrogen atmosphere, was added 2.5M butyllithium in hexane (27.9 ml). After stirring for 20 mins, the temperature was allowed to rise to 0 and redistilled phenyl cyanate (6.6 g) was added and the reaction flask placed in an ice bath. The mixture was stirred for 1 hour, and then cooled to −70°. Hydrochloric acid (2N; 20 ml) was added and the temperature allowed to rise to 0°. The mixture was poured into water, made neutral with more hydrochloric acid, and extracted with ethyl acetate. The extract was worked up to give $N^4$-(4-chlorobenzyl)-2-cyano-$N^1,N^1,N^4$-trimethyl-1H-imidazole-1,4-disulphonamide, mp 162°–163°. (compound 8)

In a similar manner, the following compounds of formula I, where X=CH, $R^1$=SO$_2$NMe$_2$, $R^2$=CN and $R^4$=Ar-W$_n$-(N=1), were obtained.

| Cpd. No | Ar | W | $R^3$ | mp (°) |
|---|---|---|---|---|
| 9 | 4-Cl—Ph | CH$_2$ | CH$_2$Ph | 123–5 |
| 10 | 2-thienyl | CH$_2$ | Me | 112–5 |
| 11 | Ph | CH$_2$ | Me | 132–4 |
| 12 | 4-MeO—Ph | CH$_2$ | Me | 140–2 |
| 13 | 4-Me—Ph | CH$_2$ | Me | 141–4 |
| 14 | Ph | CH$_2$CH$_2$ | Me | 167–8 |
| 15 | Ph | CH$_2$ | Pr$^i$ | 124–5 |
| 16 | 4-F—Ph | CH$_2$ | Me | 171–2 |
| 17 | 4-MeS—Ph | CH$_2$ | Me | 153–4 |
| 18 | 4-Cl—Ph | CH$_2$ | Et | 128–9 |
| 19 | 4-Cl—Ph | CH$_2$ | Pr | 96–7 |
| 20 | 4-Me$_2$N—Ph | CH$_2$ | Me | 159.5–61 |
| 21 | 4-Cl—Ph | CH(Me) | Me | 158.5–9.5 |

| Cpd. No | Ar | W | R³ | mp (°) |
|---|---|---|---|---|
| 22 | 4-Cl—Ph | CH₂ | 4-EtO—Ph | 107.5-9 |

PREPARATION OF THE STARTING MATERIALS

Triethylamine (92 ml) was added to a vigorously stirred solution of imidazole-4-sulphonyl chloride (99.6 g) in dichloromethane (800 ml). The mixture was cooled on an ice/water bath, stirred overnight at room temperature, filtered and the precipitate washed in turn with acetone, water and acetone and dried to give crude diimidazo-[1,5-b;1',5'-e][1,4,2,5]dithiadiazine 4,4,9,9-tetraoxide.

A mixture of this product (43.5 g) in toluene (500 ml) and 4-chlorobenzylamine (46.7 g) was heated under reflux overnight. It was then cooled and the precipitate collected, washed with toluene and light petroleum and dissolved in aqueous sodium hydroxide. The solution was washed with ether and acidified to give N-(4-chlorobenzyl)-1H-imidazole-4-sulphonamide, mp 196°-198°. (formula V).

Potassium carbonate (15.9 g) was added, with stirring, to a solution of this product (27.2 g) in acetone (300 ml). The mixture was stirred for 15 minutes at reflux and dimethylsulphamoyl chloride (16.5 g) added. The mixture was heated under reflux for 3 hours and filtered. The filtrate was cooled, evaporated under reduced pressure, and the residue suspended in water. The mixture was filtered and the solid which remained was washed with water, dried and recrystallised from toluene to give $N^4$-(4-chlorobenzyl)-$N^1$,$N^1$-dimethyl-1H-imidazole-1,4-disulphonamide, mp 171°-173°. (formula IV).

To a solution of this product (29.0 g) in dimethylformamide (300 ml) was added sodium hydride [2.53 g of 80% suspension in oil). The solution was stirred for 15 minutes at room temperature, iodomethane (11.95 g) added and the mixture stirred at room temperature for one hour.

It was poured into ice/water, filtered and the precipitate washed with water, dried and recrystallised from toluene/hexane to give $N^4$-(4-chlorobenzyl)-$N^1$,$N^1$,$N^4$-trimethyl-1H-imidazole-1,4-disulphonamide, mp 112-114°. (formula II)

In a similar manner the various intermediates to compounds 9 onwards were obtained. In the case of compounds 14, 15 17, 20 and 21, diimidazo-[1,5-b;1',5'-e][1,4,2,5]-dithiadiazine 4,4,9,9-tetraoxide was reacted with the appropriate secondary amine to give the intermediates of formula III which were then treated with dimethylsulphamoyl chloride to give the intermediate of formula II.

The melting points for the various intermediates are as follows:

| Compound No | Type A | Type A1 | Type B | Type C |
|---|---|---|---|---|
| 9 | 196-8 | | 171-3 | N.D. |
| 10 | 175-6 | | N.D. | 104-7 |
| 11 | N.D. | | N.D. | 102-4 |
| 12 | N.D. | | N.D. | N.D. |
| 13 | N.D. | | N.D. | N.D. |
| 14 | | 147.5-8.5 | | 120-2 |
| 15 | | 209.5-10.5 | | 135-6 |

| Compound No | Type A | Type A1 | Type B | Type C |
|---|---|---|---|---|
| 16 | 182-4 | | 183-7 | 130.5-2 |
| 17 | | 188.5-9.5 | | 126-7 |
| 18 | N.D. | | N.D. | 108-9 |
| 19 | N.D. | | N.D. | 125.5-6.5 |
| 20 | | 190-3 | | 150-0.5 |
| 21 | | 168-70 | | 138-40 |
| 22 | 209-12 | | 176-8 | 125-6 |

N.D. = not determined

EXAMPLE 4

A mixture of compound 17 (100 mg) in dichloromethane (10 ml) and m-chloroperbenzoic acid (73 mg of 55%), containing a few beads of 4Å molecular sieve, was stirred at room temperature for 0.5 hours. The mixture was washed with aqueous sodium metabisulphite and aqueous sodium bicarbonate, dried and evaporated. The residue was recrystallised from ethyl acetate/light petroleum to give $N^4$-(4-methylsulphinylbenzyl)-2-cyano-$N^1$,$N^1$,$N^4$-trimethyl-1H-imidazole-1,4-disulphonamide, mp 126°. (compound 23).

In a similar manner, but using approximately three times the equivalent amount of m-chloroperbenzoic acid and a reaction time of 2 hours there was obtained $N^4$-(4-methylsulphonylbenzyl)-2-cyano-$N^1$,$N^1$,$N^4$-trimethyl-1H-imidazole-1,4-disulphonamide, mp 169°-172°. (compound 24).

TEST EXAMPLE

The compounds of the invention were subjected to various tests.

Compounds are assessed for activity against *Phytophthora infestans* (late tomato blight-PI) and *Plasmopara viticola* (vine downy mildew-PV).

Aqueous solutions or dispersions of the compounds at the desired concentration, including a wetting agent, were sprayed onto the appropriate plant and then inoculated by spraying with spore suspensions of the fungi. Plants were then kept under controlled environment conditions suitable for maintaining plant growth and development of the disease. After an appropriate time, the degree of infection of the leaf surface was visually estimated.

Compounds were considered active if they gave greater than 50% control of the disease at a concentration of 125 ppm (w/v) or less. Compound 1 to 18 were active against both diseases.

We claim:

1. A compound of the formula

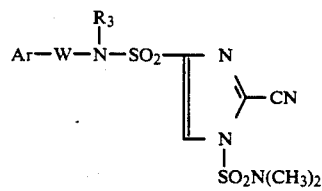

in which W is $C_{1-6}$ alkylene optionally substituted by $C_{1-8}$ allyl, $C_{3-4}$ alkenyl or $C_{3-4}$ alkynyl and Ar is phenyl, optionally substituted by halogen, $C_{1-4}$-alkyl, $C_{1-4}$-alkoxy, $C_{1-4}$-alkylthio, $C_{1-4}$-alkylsulphinyl, $C_{1-4}$-alkylsulphonyl or $C_{1-4}$-dialkylamino, or is thienyl, and $R_3$ is $C_{1-4}$alkyl.

2. A compound according to claim 1, in which W is methylene.

3. A compound according to claim 2, in which $R^3$ is methyl.

4. $N^4$-(4-Chlorobenzyl)-2-cyano-$N^1,N^1,N^4$-trimethyl-1H-imidazole-1,4-disulphonamide.

5. $N^4$-(4-Fluorobenzyl)-2-cyano-$N^1,N^1,N^4$-trimethyl-1H-imidazole-1,4-disulphonamide.

6. $N^4$-Benzyl-2-cyano-$N^1,N^1,N^4$-trimethyl-1H-imidazole-1,4-disulphonamide.

7. $N^4$-(4-Methylbenzyl)-2-cyano-$N^1,N^1,N^4$-trimethyl-1H-imidazole-1,4-disulphonamide.

8. A fungicidal composition comprising a fungicidally effective amount of a compound as claimed in claim 1, in admixture with an agriculturally acceptable diluent or carrier.

9. A method of combating phytopathogenic fungi which comprises applying to the fungus or its locus a fungicidally effective amount of a compound claimed in claim 1.

10. A method of combating phytopathogenic fungi which comprises applying to the fungus or its locus a fungicidally effective amount of a compound claimed in claim 2.

11. A method of combating phytopathogenic fungi which comprises applying to the fungus or its locus a fungicidally effective amount of a compound claimed in claim 5.

12. A method of combating phytopathogenic fungi which comprises applying to the fungus or its locus a fungicidally effective amount of a compound claimed in claim 4.

13. A fungicidal composition comprising a fungicidally effective amount of a compound as claimed in claim 2, in admixture with an agriculturally acceptable diluent or carrier.

14. A fungicidal composition comprising a fungicidally effective amount of a compound as claimed in claim 5, in admixture with an agriculturally acceptable diluent or carrier.

15. A fungicidal composition comprising a fungicidally effective amount of a compound as claimed in claim 4, in admixture with an agriculturally acceptable diluent or carrier.

16. A method of combating phytopathogenic fungi which comprises applying to the fungus or its locus a fungicidally effective amount of a compound claimed in claim 6.

17. A method of combating phytopathogenic fungi which comprises applying to the fungus or its locus a fungicidally effective amount of a compound claimed in claim 7.

18. A fungicidal composition comprising a fungicidally effective amount of a compound as claimed in claim 6, in admixture with an agriculturally acceptable diluent or carrier.

19. A fungicidal composition comprising a fungicidally effective amount of a compound as claimed in claim 7, in admixture with an agriculturally acceptable diluent or carrier.

* * * * *